(12) United States Patent
Kluczynski

(10) Patent No.: US 7,324,204 B2
(45) Date of Patent: Jan. 29, 2008

(54) METHOD AND APPARATUS FOR TRACE GAS DETECTION

(75) Inventor: Pawel Kluczynski, Västra Frölunda (SE)

(73) Assignee: Siemens Aktiengesellschaft, Munich (DE)

( * ) Notice: Subject to any disclaimer, the term of this patent is extended or adjusted under 35 U.S.C. 154(b) by 143 days.

(21) Appl. No.: 11/358,854

(22) Filed: Feb. 21, 2006

(65) Prior Publication Data

US 2006/0192967 A1    Aug. 31, 2006

(30) Foreign Application Priority Data

Feb. 22, 2005    (EP)    ................................. 05003771

(51) Int. Cl.
     *G01N 21/61*    (2006.01)

(52) U.S. Cl. ..................................................... 356/437

(58) Field of Classification Search ........ 356/432–440; 250/345, 343, 339.13
See application file for complete search history.

(56) References Cited

U.S. PATENT DOCUMENTS

| | | | |
|---|---|---|---|
| 4,583,859 A * | 4/1986 | Hall, II | ....................... 356/438 |
| 5,177,561 A | 1/1993 | Milosevic et al. | |
| 5,517,314 A * | 5/1996 | Wallin | ......................... 356/437 |
| 5,747,809 A | 5/1998 | Eckstrom | |
| 6,040,914 A | 3/2000 | Bortz et al. | |
| 6,040,915 A | 3/2000 | Wu et al. | |
| 6,369,387 B1 | 4/2002 | Eckles | |
| 6,444,985 B1 * | 9/2002 | Mori et al. | ............ 250/339.13 |
| 6,635,875 B1 | 10/2003 | Bley et al. | |
| 6,791,689 B1 * | 9/2004 | Weckstrom | .................. 356/437 |
| 7,251,034 B2 * | 7/2007 | Kluczynski et al. | ......... 356/437 |
| 2005/0122523 A1 * | 6/2005 | Yan | ............................ 356/437 |

FOREIGN PATENT DOCUMENTS

EP      1 092 971 A2    4/2001

* cited by examiner

*Primary Examiner*—Hoa Q. Pham

(57) ABSTRACT

In spectroscopic devices the sections of an optical measuring path from a light source to a measuring volume containing a measuring gas and from there to a measuring detector are often sealed off from the ambient atmosphere and purged with a purge gas such as dry nitrogen to prevent penetration of atmospheric gas components, such as water vapor, which may interfere with the trace gas measurement. The moisture content in the nitrogen supply is usually in the range of a few ppm at the gas source and can increase dramatically at the measuring site depending on the length of the nitrogen pipe net and due to porosity of the pipe walls, leakage of seals and residual moisture trapped in so-called dead legs. In order to compensate interfering absorption of atmospheric gas components and other impurities in the purge gas the purge gas is collected after flushing the optical path sections, a portion of the light of the light source is transmitted along a second optical path to a compensation detector, the second optical path is flushed with the collected purge gas and the trace gas component in the measuring gas is determined based on a difference between the output of the measuring detector and the output of the compensation detector.

4 Claims, 1 Drawing Sheet

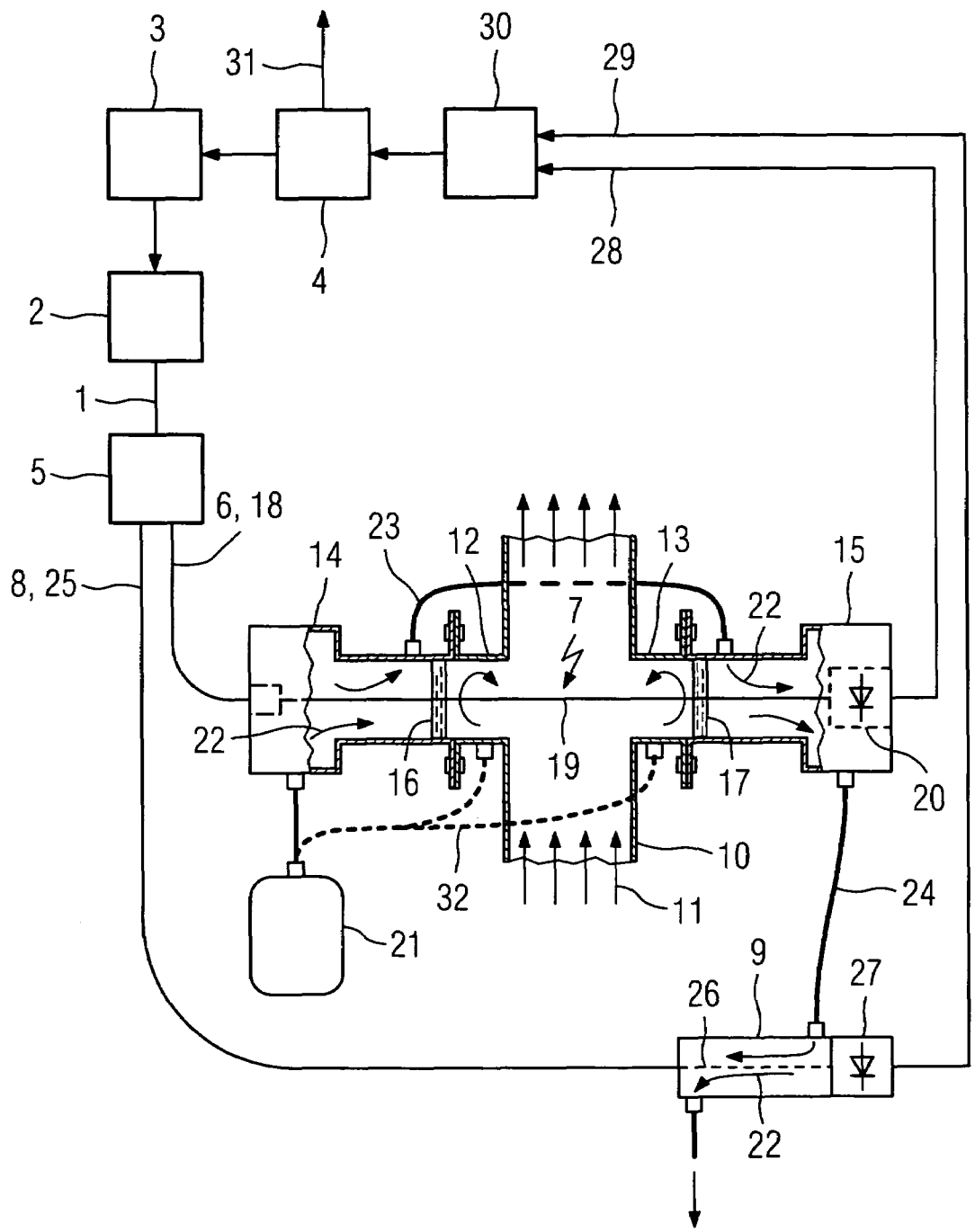

METHOD AND APPARATUS FOR TRACE GAS DETECTION

CROSS REFERENCE TO RELATED APPLICATION

This application claims priority of the European application No. 05003771.2 EP filed Feb. 22, 2005, which is incorporated by reference herein in its entirety.

FIELD OF THE INVENTION

The invention relates to a method for quantitatively determining a trace gas component in a measuring gas.

It further relates to a corresponding apparatus.

BACKGROUND OF THE INVENTION

In spectroscopic trace gas detection, the concentration of a known gas component, or gas components, in a gas mixture (measuring gas) is determined from a measured wavelength-specific absorption of the gas component or a measured absorption spectrum of the measuring gas, respectively. For this purpose, the measuring gas is introduced in a measuring volume having a predetermined optical measurement path length, e.g. a sample cell or, in case of in-situ process measurements, a gas-leading pipe, furnace, funnel or the like. The light of a light source, e.g. an infrared lamp or a tunable diode laser, is transmitted through the measuring volume to a measuring detector, e.g. an opto-pneumatic or solid-state detector, for generating a measuring detector output dependent on the light absorption in the optical path of the measuring volume. In dual-cell or dual-beam devices, a portion of the light of the light source is passed through a reference cell comprising the known gas component or another suitable gas component of constant concentration. Afterwards the light is detected by a reference detector, the output of which is used for self-calibration and zero point determination of the system.

Trace gas detection in a measuring gas with high precision and sensitivity is very difficult if the main ingredient or ingredients of the measuring gas and the trace gas component to be measured absorb light at identical wavelengths and if the amount of absorption by the main ingredient is greater than that by the trace gas component. An example is the quantitative analysis of moisture (water vapor) in process gases like ammonia or nitrogen. To eliminate such interfering absorption, it has been proposed in U.S. Pat. No. 6,040,914 to introduce into the reference cell a cancel gas consisting of the main ingredient of the measuring gas without the trace gas component, e.g. dry ammonia or dry nitrogen, and to subtract the absorption spectrum of the cancel gas from the absorption spectrum of the measuring gas by subtracting the output of the reference detector from the output of the measuring detector.

From U.S. Pat. No. 6,635,875 a gas analyzer for leak detection is known, wherein a gas sample is taken by a sampling probe and led into an infrared sample cell, where the light absorption of the gas sample is measured. As the sampling probe not only collects gases escaping from a possibly existing leak but also gases from the environment of the probe, atmospheric gases from the environment of the sampling probe's tip are taken by an additional reference probe and fed into a reference cell, where the light absorption of the atmospheric gases is measured. By subtracting the measured light absorption of the atmospheric gases from the measured absorption of the gas sample, a proper leak detection is achieved.

In spectroscopic devices, such as known from U.S. Pat. No. 5,177,561, the optical path from the light source to the measuring volume and from there to the measuring detector is often sealed off from the ambient atmosphere and purged with a purge gas such as dry nitrogen to prevent penetration of atmospheric gas components, e.g. water vapor, which may interfere with the trace gas measurement. The moisture content in the nitrogen supply is usually in the range of a few ppm at the gas source and can increase dramatically at the measuring site depending on the length of the nitrogen pipe net and due to porosity of the pipe walls, leakage of the seals and residual moisture trapped in so-called dead legs.

U.S. Pat. No. 5,747,809 discloses an NDIR apparatus and method for measuring an analyte in a gaseous sample. For this purpose the light of a light source is split to pass through at least one sample cell containing the sample and at least one reference cell free of said analyte. The reference cell therefore contains a purge gas, which may circulate through a trap for removing any traces of the analyte. After having left the reference cell and before being purified in the trap, the circulating gas may be used to flush sections of the optical paths between the light source and the sample and reference cells and between them and a detector, so that any traces of the analyte will be removed from there and later captured by the trap.

SUMMARY OF THE INVENTION

The invention seeks to provide a trace gas detection method and apparatus which compensate interfering absorption of atmospheric gas components and other impurities in the purge gas.

According to the invention this is achieved by the method defined in the claims and the apparatus defined in the claims.

Preferred embodiments of the method and apparatus according to the invention are specified in the remaining claims.

In accordance with the invention the light absorption of the purge gas after purging the optical path from the light source to the measuring volume and from there to the measuring detector is measured and subtracted from the measured light absorption of the measuring gas. Thus, any offset in the quantitatively determined trace gas level caused by impurities in the purge gas will be automatically and in real-time compensated. By this means the trace gas detection limit and accuracy are significantly improved. Additionally, the compensation is effective even in cases when the pressure and absorption line broadening in the measuring gas and in the purge gas are different.

In order to improve the accuracy of the measurement the measured light absorptions of the measuring gas and the purge gas are adjusted prior to their subtraction by means of a scaling factor, which depends on the ratio of the purged optical path length in the measuring volume and the purged length of the second optical path and which can be obtained from design data of the apparatus or can be measured when the measuring volume is filled with the purge gas.

BRIEF DESCRIPTION OF THE DRAWING

The invention will be now described by way of a preferred example and with reference to the only FIGURE of the drawing.

FIG. 1—FIG. 1 provides a detailed view of the preferred embodiment.

DETAILED DESCRIPTION OF THE INVENTION

Light 1 having a suitable wavelength for spectroscopic gas analysis is emitted from a light source 2, here a tunable diode laser, which is driven by a laser controller 3. The laser controller 3 controls the injection current and/or the temperature of the diode laser 2 according to information provided by a computer 4 so as to continuously vary the wavelength of the emitted light 1 over a desired wavelength range for analysis. The light 1 is split by means of an optical coupler 5 into a first portion 6 for passing through a measuring volume 7 and a second portion 8 for passing through a compensation volume 9.

In the shown example the measuring volume 7 is part of a gas pipe 10 through which a process gas, the measuring gas 11, flows. The measuring gas 11 may be chlorine, the moisture content of which has to be determined. Two flange tubes 12 and 13 are welded at diametrically opposed positions into the wall of the gas pipe 10. A transmitter unit 14 and a receiver unit 15 are mounted to the respective flange tubes 12 and 13, the interiors of the units 14 and 15 being separated from the interior of the gas pipe 10 by optical windows 16 and 17. The first light portion 6 is guided by a first fiber optic cable 18 from the optical coupler 5 to the transmitter unit 14. From there the first light portion 6 is transmitted along a first optical path 19 through the flange tubes 12, 13 and the intermediate measuring volume 7 to the receiving unit 15, where it impinges onto a measuring detector 20. The interior of the transmitter unit 14 is connected to a purge gas source 21 for flushing the sections of the first optical path 19 running through the units 14 and 15 with a purge gas 22 such as nitrogen, thus defining the remaining unpurged section within the gas pipe 10 as the measurement path length. For this purpose the purge gas 22 is conducted from the interior of the transmitter unit 14 to the interior of the receiver unit 15 by means of a gas feed line 23. Of course the optical path sections to be purged can be flushed in other, different orders and directions.

After flushing the first optical path sections the purge gas 22 is transferred via a further gas feed line 24 to and conducted through the compensation volume 9, here a compensation cell having a predetermined optical path length. The second light portion 8 is guided by a second fiber optic cable 25 from the optical coupler 5 to the compensation volume 9, where it is transmitted along a second optical path 26 through the compensation volume 9 to a compensation detector 27.

The wavelength of the light 1 of the light source 2 is continuously scanned over a characteristic absorption line of the trace gas component to be measured, here water vapor. Thus, the measuring detector output 28 contains the wavelength-specific light absorption of the moisture content of both the measuring gas 11 and the purge gas 22, whereas the compensation detector output 29 only contains the light absorption of the moisture content of the purge gas 22. The detector outputs 28 and 29 are fed to an evaluation means 30 which determines the moisture content of the measuring gas from the difference between the measuring detector output 28 and the compensation detector output 29. The determined moisture content is then provided via an output 31 of the computer 4 for displaying or further processing.

As indicated by dotted lines 32, a portion of the purge gas 22 coming from the gas source 21 can be fed into the respective interiors of the flange tubes 12 and 13. The purge gas flow helps to remove measuring gas 11 from dead areas and to keep the optical windows 16 and 17 cool and clean, the latter by preventing the windows 16 and 17 from coming into contact with dust and furnace-off gases flowing through the gas pipe 10.

Many other modifications and variations of the invention are possible in view of the above disclosure. So instead of the optical coupler 5 a beam splitter might split the light 1 of the light source 2 into a first light beam passing through the measuring volume 7 and a second light beam for passing through the compensation volume 9. Furthermore, the invention can be applied to other known absorption-based measuring principles.

The invention claimed is:

1. A method for quantitatively determining a trace gas component in a measuring gas, comprising:
    introducing the measuring gas into a measuring volume;
    emitting light from a light source;
    passing a first portion of the light along a first optical path from the light source through the measuring volume to a measuring detector;
    generating a measuring detector output dependent on the light absorption in the first optical path;
    flushing sections of the first optical path between the light source and the measuring volume and the measuring volume and the measuring detector with a purge gas;
    collecting the purge gas after flushing the first optical path sections;
    transmitting a second portion of the light along a second optical path from the light source to a compensation detector;
    flushing the second optical path with the collected purge gas;
    generating a compensation detector output dependent on the light absorption in the second optical path; and
    determining the trace gas component in the measuring gas based on a difference between the measuring detector output and the compensation detector output.

2. The method of claim 1, further comprising the step of varying the frequency of the light of the light source over a frequency spectrum including an absorption frequency of the trace gas component.

3. The method of claim 1, further comprising the step of prior to determining the trace gas component adjusting the ratio of the measuring and compensation detector outputs by a scaling factor, wherein said scaling factor depends on the ratio of the purged optical path length in the measuring volume and the purged length of the second optical path.

4. An apparatus for quantitatively determining a trace gas component in a measuring gas, comprising:
    a measuring volume configured to contain the measuring gas;
    a light source;
    a device for obtaining a first portion and a second portion of the light from the light source;

a measuring detector for generating a measuring detector output;

a device for passing the first light portion along a first optical path through the measuring volume to the measuring detector;

a compensation detector for generating a compensation detector output;

a device for transmitting the second light portion along a second optical path to the compensation detector;

a device for providing a purge gas;

a device for flushing sections of the first optical path between the light source and the measuring volume and the measuring volume and the measuring detector with the purge gas;

a device for collecting the purge gas after flushing the first optical path sections;

a device for flushing the second optical path with the collected purge gas; and evaluation device for determining the trace gas component in the measuring gas based on a difference between the measuring detector output and the compensation detector output.

* * * * *